United States Patent
Yasushi et al.

(10) Patent No.: US 9,820,826 B2
(45) Date of Patent: Nov. 21, 2017

(54) ULTRASONIC TIP FOR ULTRASONIC INSTRUMENT AND METHOD OF DENTAL TREATMENT WITH SAID ULTRASONIC TIP

(71) Applicant: SOCIETE POUR LA CONCEPTION DES APPLICATIONS DES TECHNIQUES ELECTRONIQUES, Merignac (FR)

(72) Inventors: Yoda Yasushi, Tokyo (JP); Vianney Ruellan, Bordeaux (FR); Jean-Michel Richer, Bruges (FR)

(73) Assignee: SOCIETE POUR LA CONCEPTION DES APPLICATIONS DES TECHNIQUES ELECTRONIQUES, Merignac (FR)

( * ) Notice: Subject to any disclaimer, the term of this patent is extended or adjusted under 35 U.S.C. 154(b) by 248 days.

(21) Appl. No.: 14/493,584

(22) Filed: Sep. 23, 2014

(65) Prior Publication Data
US 2016/0081764 A1 Mar. 24, 2016

(51) Int. Cl.
A61C 1/07 (2006.01)
A61C 3/03 (2006.01)
A61C 8/00 (2006.01)
A61C 17/20 (2006.01)

(52) U.S. Cl.
CPC .......... *A61C 1/07* (2013.01); *A61C 3/03* (2013.01); *A61C 8/0089* (2013.01); *A61C 17/20* (2013.01)

(58) Field of Classification Search
USPC ........................................... 433/119
See application file for complete search history.

(56) References Cited

U.S. PATENT DOCUMENTS

2003/0096213 A1  5/2003  Hickok et al.
2008/0248444 A1  10/2008  Bahcall et al.
(Continued)

FOREIGN PATENT DOCUMENTS

EP    1747766 B1    10/2010
KR    100818730 B1   4/2008
(Continued)

OTHER PUBLICATIONS

International Search Report from PCT Application No. PCT/EP2015/071545, dated Sep. 21, 2015.

*Primary Examiner* — Nicole F Johnson
(74) *Attorney, Agent, or Firm* — Workman Nydegger (57) ABSTRACT

The invention provides an ultrasonic tip in titanium for ultrasonic instrument, and further provides a method of dental treatment of peri-implantitis using an ultrasonic tip operable to cooperate with an ultrasonic instrument to transmit ultrasonic vibrations to a surface of a dental implant to be treated, said implant and said ultrasonic tip being made of titanium. The present invention guarantees a safe and complete debridement of most implants for the dental treatment of peri-implantitis, and for the maintenance of the implant surface after such a treatment. Designed in pure titanium, like most dental implant in the market, the tip of the present invention advantageously avoids the transfer of material on the implant and the alteration of the surface, thereby preventing the risk of bacterial recontamination.

19 Claims, 5 Drawing Sheets

(56) References Cited

U.S. PATENT DOCUMENTS

2009/0202961 A1* 8/2009 Fani .................. A61C 1/088
433/119
2010/0240006 A1* 9/2010 Kwon ................. A61C 3/03
433/143

FOREIGN PATENT DOCUMENTS

| WO | 2013030563 A1 | 3/2013 |
| WO | 2014042665 A1 | 3/2014 |

* cited by examiner

ULTRASONIC TIP FOR ULTRASONIC INSTRUMENT AND METHOD OF DENTAL TREATMENT WITH SAID ULTRASONIC TIP

BACKGROUND OF THE INVENTION

The invention pertains to ultrasonic dental instruments. More specifically, the invention provides ultrasonic tips for such instruments.

The invention is particularly applicable in the periodontal treatment of dental implants.

Recently, the increasing occurrence of peri-implant disease has been reported due to the rapid increase of dental implant therapy throughout the world. In peri-implantitis, exposed fixture surfaces of dental implants that lose osseointegration with the supportive bone are contaminated by bacterial biofilms and/or mineralized deposits.

To treat peri-implantitis, it is necessary to decontaminate the exposed contaminated fixture surfaces of the dental implant. Ultrasonic technology has been reported as an effective method for the treatment of peri-implant disease.

As known to those skilled in the art, most of the dental implants today are in titanium. However, the elements of different electron potential on the titanium implant surface cause the risk of fixture erosion, and the optimal materials of ultrasonic tip for debridement of microstructured surfaces of titanium implants have not been properly evaluated yet.

In addition, existing ultrasonic instruments for the treatment of peri-implantitis are not satisfactory.

Accordingly, there is a strong need for an ultrasonic system allowing safe and complete debridement of implants for the treatment of peri-implantitis. There is more particularly a need for an ultrasonic tip which, when mounted on an ultrasonic instrument, allows for optimal results in the treatment of infected dental implants.

SUMMARY OF THE INVENTION

The present invention provides a method of dental treatment of peri-implantitis using an ultrasonic tip operable to cooperate with an ultrasonic instrument to transmit ultrasonic vibrations to a surface of a dental implant to be treated, wherein said implant and said ultrasonic tip are in titanium.

The method of the present invention guarantees a safe and complete debridement of most implants for the dental treatment of peri-implantitis, and for the maintenance of the implant surface after such a treatment.

Designed in pure titanium, like most dental implant in the market, the tip of the present invention advantageously avoids the transfer of material on the implant and the alteration of the surface, thereby preventing the risk of bacterial recontamination.

In a particular embodiment, the ultrasonic tip is of the grade 4 type according to the standards ISO 5832-2 and ASTM F-67.

In a particular embodiment, the implant surface includes a threading region comprising a plurality of threads, the distal end of the ultrasonic tip being shaped to be in correspondence with the profile of a recessed region between each pair of threads within the threading region.

In a particular embodiment, the structural specifications of the ultrasonic tip are arranged such that said ultrasonic tip has a unique resonance frequency which falls within the operating frequency range of said ultrasonic instrument.

In a particular embodiment, the unique resonance frequency at which are transmitted the ultrasonic vibrations to the implant surface is comprised between 30 kHz and 34 kHz.

The present invention also provides an ultrasonic tip operable to cooperate with an ultrasonic instrument to vibrate at an ultrasonic frequency for use in dental treatment of peri-implantitis on a dental implant, wherein said ultrasonic tip is in titanium.

In a particular embodiment, the ultrasonic tip is made of titanium of the grade 4 type according to the standards ISO 5832-2 and ASTM F-67.

In a particular embodiment, the distal end of the ultrasonic tip is formed so as to have any one of a pointed shape, a half-spherical shape and a curved shape.

The present invention also provides an ultrasonic system for treatment of peri-implantitis, the ultrasonic system comprising:

an ultrasonic tip as defined above; and
an ultrasonic instrument operable to transmit ultrasonic vibrations to the ultrasonic tip when said ultrasonic tip is mechanically coupled with said ultrasonic instrument.

In a particular embodiment, the ultrasonic system further comprises an ultrasonic generator coupled with said ultrasonic instrument to supply a driving ultrasonic signal to the ultrasonic instrument so as to cause ultrasonic vibrations of said ultrasonic tip.

BRIEF DESCRIPTION OF THE DRAWINGS

The invention including preferred embodiments and advantages thereof will be described below in detail, by way of example, with reference to the accompanying drawings.

DETAILED DESCRIPTION OF PARTICULAR EMBODIMENTS OF THE INVENTION

While this invention is susceptible of embodiment in many different forms, there are shown in the drawing and will be described herein in detail specific embodiments thereto with the understanding that the present disclosure is to be considered as an exemplification of the principles of the invention and is not intended to limit the invention to the specific embodiment illustrated.

Numerous details are set forth to provide an understanding of the embodiments described herein. The exemplary embodiments may be practiced without these details. In other instances, well-known methods, procedures, and components have not been described in detail to avoid obscuring the embodiments described.

For simplicity and clarity of illustration, reference numerals may be repeated among the figures to indicate corresponding or analogous elements.

Figure 1A:
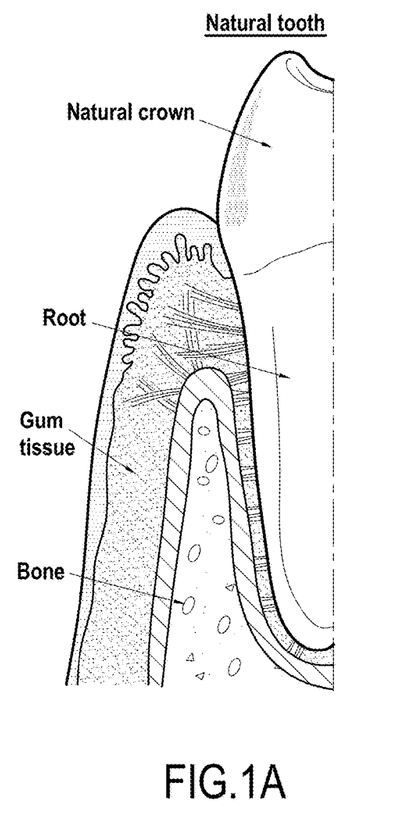
FIGS. 1A and 1B are cross-sectional views showing respectively a natural tooth and a dental implant.
Figure 1B:
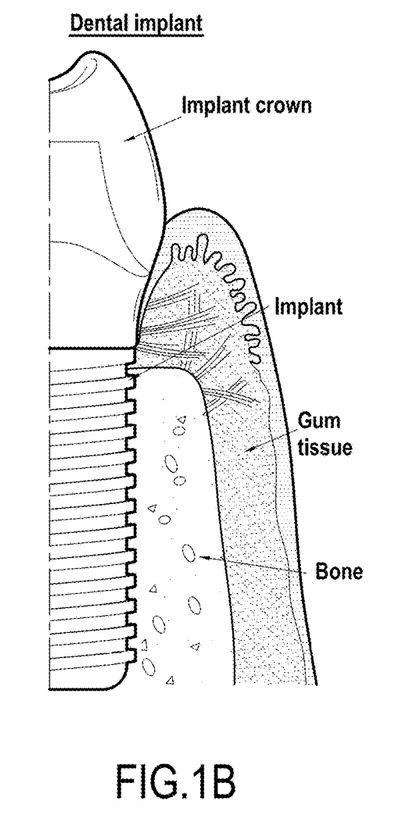

FIGS. 1A and 1B illustrate respectively a natural tooth and a dental implant in a schematic manner. As shown in FIG. 1A, the periodontal tissues naturally attach the bone to the root surfaces of the teeth; they act as a shock absorber. The gum tissues attach into the root surfaces, helping to protect the underlying bone.

As shown in FIG. 1B, titanium, of which most dental implants are made of, fuses to the jawbone giving implants great strength and stability. More particularly, the threads present at the base of the implant are designed to improve the attachment quality of the implant onto the surrounding jawbone.

However, the gum tissues cannot attach to the implants in the same manner as they do to tooth roots; instead they adhere to them tightly by a suction-type mechanism.

Dental implants usually show gaps and cavities (in particular between each thread) into which germs can penetrate from the oral cavity. In case of inflammation of the soft and hard periodontal tissues surrounding the implant due to a bacterial infection, the underlying jawbone tends to degenerate vertically and/or horizontally. Peri-implantitis is this destructive inflammatory process affecting the soft and hard tissues around the infected dental implant. The array of periodontal pathogens which can be found around failing implants (those affected by peri-implantitis) are very similar to those found in association with various forms of periodontal disease.

Adequate treatment is required to clean the infected implant surface (removal of bacterial biofilms and/or mineralized deposits etc.) and stop the inflammation so that the supportive bone and soft tissues can heal and grow back around the dental implant.

While the use of chemical treatments is known in the art, mechanical debridement is very often employed (alone or in combination) for the treatment of peri-implant diseases.

In particular, ultrasonic dental cleaning and scaling instruments have been long recognized as useful in promoting oral hygiene and more recently for the treatment of peri-implantitis.

Known ultrasonic system includes a handpiece (also called "ultrasonic instrument"). Typically, in the housing of the handpiece is provided a piezoelectric transducer (or a magnetostrictive device) for generating ultrasonic vibrations in response to a driving ultrasonic signal (e.g. 25 KHz or 30 KHz) which originates from a control unit (i.e. an ultrasonic generator). The distal end of the handpiece is configured so that an appropriate ultrasonic tip can be mounted upon, preferably in a removable manner.

The distal end of the handpiece is designed to transmit ultrasonic vibrations to the ultrasonic tip. A fluid (often water) may also be supplied from an internal canal in the handpiece into the ultrasonic tip. In operation, the extremity of the ultrasonic tip vibrates at an ultrasonic frequency and the fluid supplied from the handpiece to the ultrasonic insert can be delivered onto adjacent tooth surfaces, tissues or implant surfaces to be treated.

A particular embodiment of an ultrasonic system employing an example of a tip according to the present invention will be described in more detail later with reference to FIGS. 2-4 and FIGS. 5A-5B.

The Applicant has carried out a thorough evaluation of morphological and elemental changes induced in particular on microstructured surfaces of titanium dental endosseous implants by ultrasonic instruments using various types of conventional ultrasonic tips.

Tips used with ultrasonic instruments for treating peri-implant diseases, and more generally for treating contaminated surfaces of dental implants, were initially made of stainless steel, and more recently, made of a plastic alloy (such Peek™ for instance) or a copper alloy. Tips made of carbon are also known but for applications other than treating peri-implant diseases. Major drawbacks associated with these conventional tips have however been observed by the Applicant as explained below.

Debridement was performed on titanium dental implants using an ultrasonic instrument with a conventional tip made of stainless steel. Tests were also performed with an ultrasonic tip made for instance of carbon. Stereomicroscopy and scanning electron microscopy (SEM) were employed to observe the morphological changes of the implant surfaces (in particular the threads formed thereon) after debridement. Severe morphological changes with microcracks formation or other surface degradations were observed in many occasions on the tested implants. Foreign elements were also detected on the implant surfaces (on the threads) after debridement with conventional tips. In particular, an alarming quantity of carbon elements was observed when using carbon tips for the implant debridement.

The microcracks and the like are not desirable after debridement of implants. Additionally, the potential negative effects resulting from the contamination of implant surfaces with foreign elements (in carbon for instance) are not well understood at present.

The present invention therefore provides an ultrasonic tip for ultrasonic instrument which leads to far better results in the treatment of peri-implantitis and, in particular, prevents occurrence of mechanical damages on the implant surface and avoids the presence of foreign elements as explained above.

According to the present invention, the ultrasonic tip for ultrasonic instrument is made of a not alloyed titanium (or pure titanium), preferably titanium of the "grade 4" type as defined in the standards ISO 5832-2 and ASTM F-67 (sometimes referred simply hereafter as "grade 4" for a matter of simplicity). Reference is also made to standard ASTM B 348.

A pure titanium tip (preferably grade 4) can be advantageously mounted on an ultrasonic instrument for treatment of implant surfaces, in particular for treatment and maintenance of peri-implantitis.

Exemplary embodiments of the present invention will now be described with reference to FIGS. 2-10.

Figure 2:
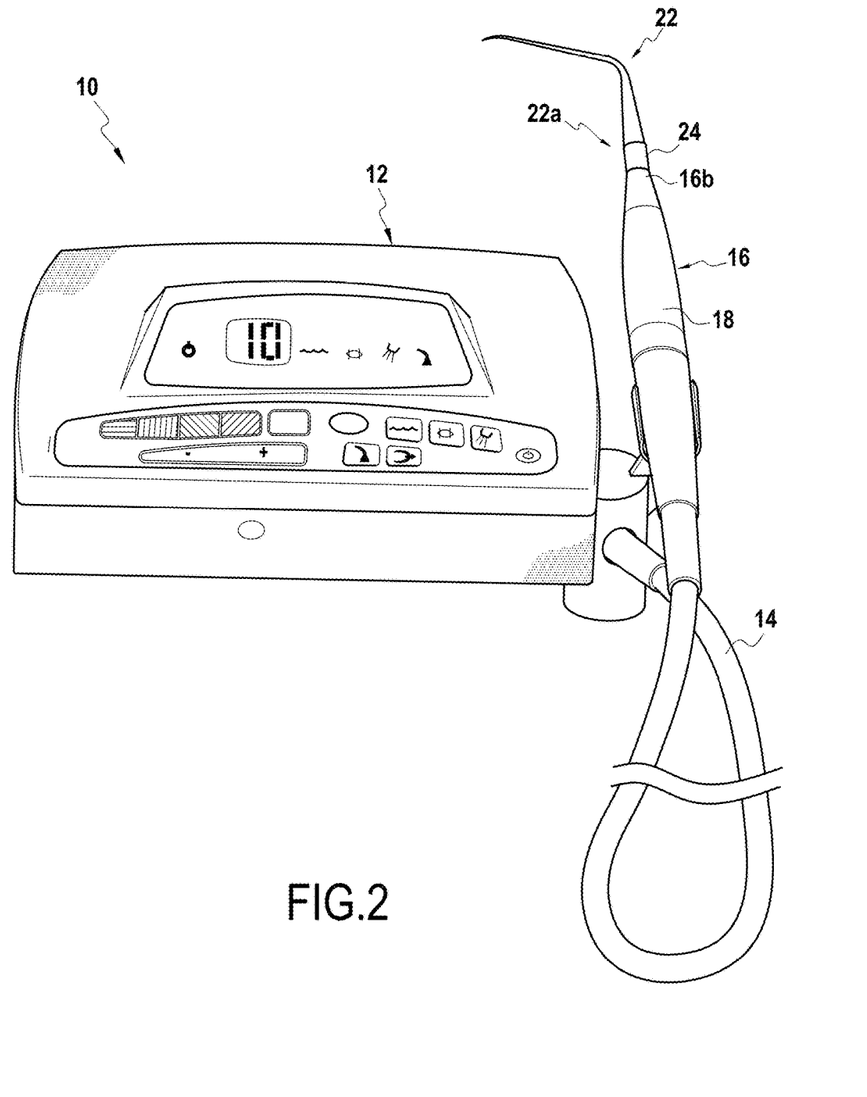
FIG. 2 is a diagram of an ultrasonic system according to a particular embodiment of the present invention.

FIG. 2 illustrates an ultrasonic system 10 including a control unit (also called ultrasonic generator) 12 of a conventional type for providing ultrasonic signals, for instance in a range of 20 to 40 kHz. In a particular embodiment, the operating frequency range within which the control unit 12 can operate is 28 kHz-36 kHz.

A cable 14 includes conductors for the electrical signals generated by the control unit 12 as well as a flow path to provide a fluid (e.g. water or some form of fluid antibiotic) to be applied to the implant surface to be treated.

The cable 14 couples the control unit 12 to a hand-piece (also named "ultrasonic instrument") 16 of the scaling system 10.

Figure 3:
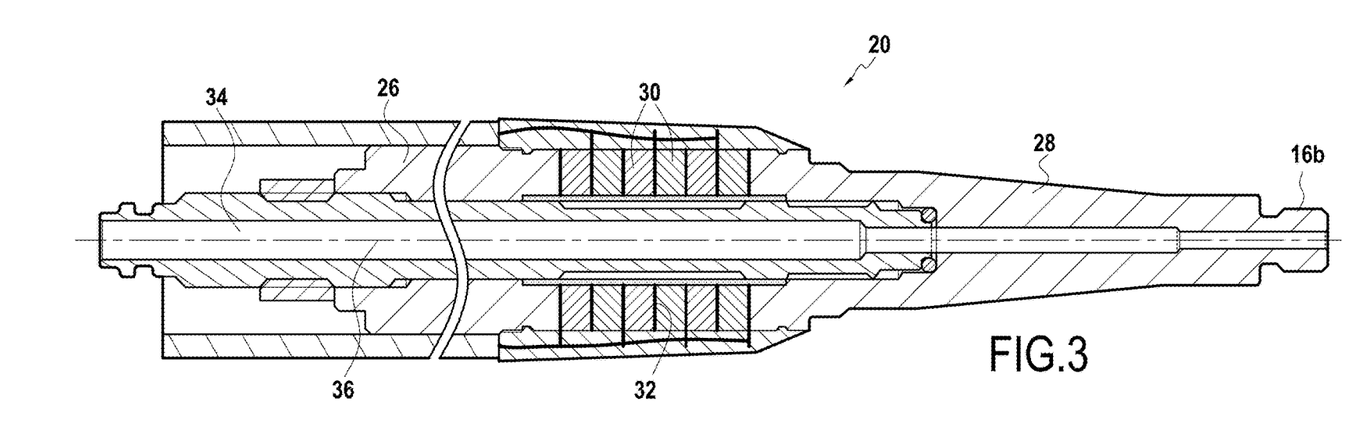
FIG. 3 is a diagrammatic longitudinal section view of part of a handpiece of an ultrasonic instrument, according to a particular embodiment of the present invention.

FIG. 3 is a cross-sectional view showing in a schematic manner the internal arrangement of a part of the handpiece 16 along the longitudinal axis thereof.

The handpiece 16 comprises a housing 18 in which a piezoelectric transducer 20 is provided in a conventional manner.

Coupled to the distal end 16b of the handpiece 16, is an ultrasonic tip 22. The base (or proximal end) 22a of tip 22 is arranged to removably engage the distal end 16b of the handpiece 16, for instance by means of conventional locking mechanism 24 also of a type known to those skilled in the art.

The ultrasonic tip 22 can be removed from the distal end of the handpiece 16 for replacement, sterilization purposes etc.

The piezoelectric transducer 20 is situated in this example between a counterweight part 26 and an amplifier part 28. The transducer 20 comprises a plurality of ceramic piezoelectric disks 30 with electrical contacts 32 interposed therebetween so as to enable the piezoelectric transducer 20 to be powered electrically by electrical signal from the control unit 12. The stack of piezoelectric disks 30 is mechanically constrained at opposite ends by the amplifier part 28 and the counterweight part 26.

In this particular example, the amplifier part 28 and counterweight part 26 are connected together by an axial prestress rod 34, the rod itself having a central conduit 36 for conveying a fluid toward the distal end 16b of the handpiece 16.

As is well known in the art, the piezoelectric transducer 16 is suitable for generating ultrasonic vibrations under the effect of electrical power being applied to the electrical contacts 32 by the control unit 12. This in turn imparts a vibratory motion of the ultrasonic tip 22 which is mechanically coupled with the distal end 16b of the transducer 16. The amplitude of vibration imparted to the ultrasonic tip 22 is a function of the power delivered by the control unit 12.

It will be understood that a variety of different embodiments of ultrasonic instruments may be used with the ultrasonic tip without departing from the spirit and scope of the present invention. Among other things, ultrasonic vibrations can alternatively be produced within the housing of the handpiece using a magnetostrictive system as is well known in the art.

The ultrasonic tip of the present invention guarantees a safe and complete debridement of most implants for the dental treatment of peri-implantitis.

Designed in pure titanium, like most dental implant in the market, the tip of the present invention advantageously avoids the transfer of material on the implant and the alteration of the surface, thereby preventing the risk of bacterial recontamination.

The ultrasonic tip of the present invention may be employed for surgical and/or non-surgical treatment and maintenance of peri-implantitis. Under certain circumstances, it is not necessary to surgically incise the gum tissue to access the implant surface to be treated. The ultrasonic tip may be directly applied on the accessible implant surface to perform debridement on the regions of interest. In this particular case, the treatment can be referred as a non-surgical treatment in the sense that it is not invasive for the patient.

On the other hand, it is sometimes necessary for the dentist practitioner to surgically incise the gum tissue in order to access an implant surface of interest. In that case, the treatment can be referred to as a surgical treatment in the sense that it is invasive for the patient.

The efficiency of various tips of the present invention has been confirmed by microscopic observations.

The present invention thus provides an ultrasonic tip as defined above, this ultrasonic tip being operable to cooperate with an ultrasonic instrument for use in dental treatment of peri-implantitis on a dental implant.

The present invention also provides a dental treatment of peri-implantitis using an ultrasonic tip as defined above, and more particularly, such an ultrasonic tip operating in cooperation with an ultrasonic instrument an embodiment of which has been described earlier.

In a particular aspect of the invention, the ultrasonic tip is in titanium, preferably of the grade 4 type (according to the standards ISO 5832-2 and ASTM F-67), and the treatment is for treating a contaminated surface of a titanium implant surface.

In a particular aspect of the invention, the dental treatment includes imparting ultrasonic vibrations on the ultrasonic tip from the ultrasonic instrument, and physically applying the ultrasonic tip on the implant surface for debridement.

Figure 4:
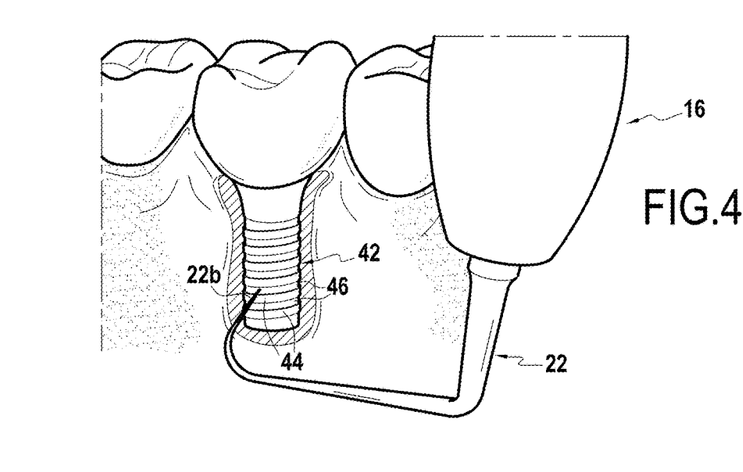
FIG. 4 shows treatment of peri-implantitis using an ultrasonic tip according to a particular embodiment of the present invention.

FIG. 4 illustrates a treatment of peri-implantitis using scaler tip 22 on the surface of a dental implant 42.

The shape and dimensions of the ultrasonic tip of the present invention should be chosen appropriately in order to achieve optimal results when cleaning implants. The working (or distal) end 22b of the ultrasonic tip may take various shapes and sizes. Using tip extremities with different diameters allow the debridement to the bottom of threads 44 (within the recessed region 46 formed between each pair of threads 44) on the implant surface, whatever the width of the threads 44.

In a particular embodiment, the ultrasonic tip includes one elongated member or a plurality of elongated portions connected to each other.

In a particular embodiment, the implant surface of interest includes a threading region comprising a plurality of threads, the distal end 22b of the ultrasonic tip being shaped to be in correspondence with the profile of a recessed region between each pair of threads within the threading region.

In a particular embodiment, the distal end of the ultrasonic tip is formed so as to have any one of a pointed shape, a half-spherical shape and a curved shape.

Figure 8:
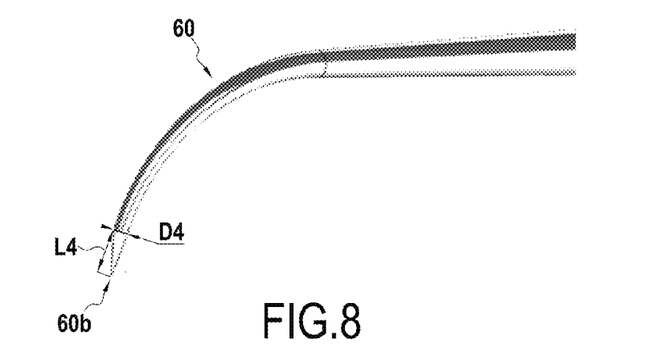
FIGS. 8, 9 and 10 show various arrangements of the distal end of an ultrasonic tip according to particular embodiments.
Figure 9:
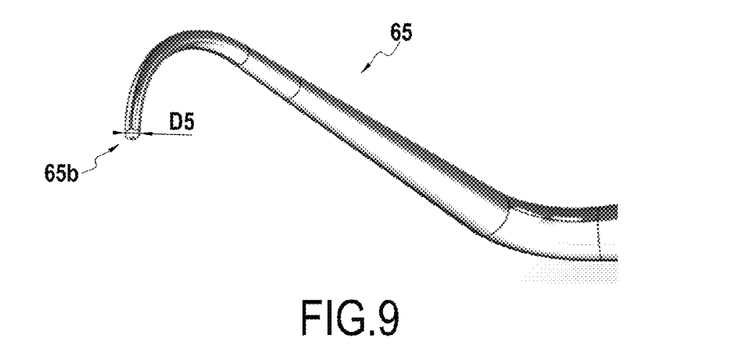
Figure 10:
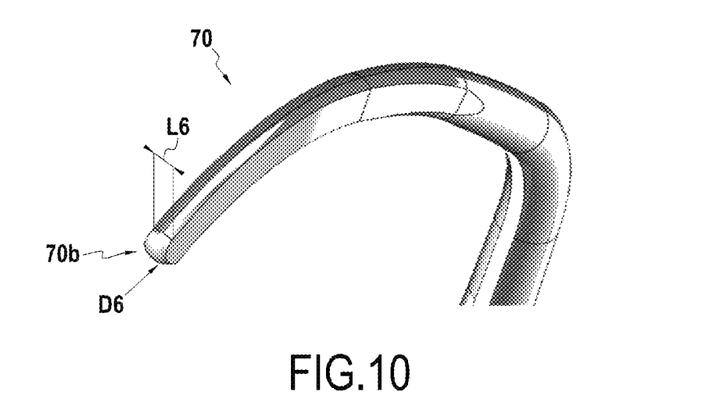

FIGS. 8, 9 and 10 show different arrangements of the distal end of the ultrasonic tip according to particular embodiments of the present invention.

More specifically, FIG. 8 illustrates an ultrasonic tip 60 according to a particular embodiment wherein the distal end 60b of the ultrasonic tip 60 has a pointed shape (formed for instance by a conic portion having a base diameter D4=0.3 mm and a height L4=1 mm). This particular shape allows easy access within very small inter-thread space.

FIG. 9 illustrates an ultrasonic tip 65 according to another embodiment wherein the distal end 65 thereof has a half-spherical shape with a diameter D5=0.3 mm.

FIG. 10 illustrates an ultrasonic tip 70 according to still another embodiment wherein the distal end 70b thereof shows two flat surfaces opposed to each other and spaced apart by a distance L6=0.6 mm, and a rounded shape such that diameter D6 as defined in FIG. 10 is set as follows: D6=0.6 mm.

In a particular embodiment, the ultrasonic tip 22 is shaped with an adequate curvature to facilitate access and passage around the implant for a total decontamination.

Figure 5A:
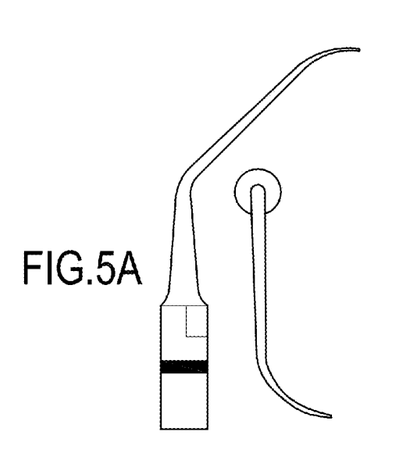
FIGS. 5A and 5B show exemplary embodiments of an ultrasonic tip according to the present invention.

For instance, a tip with a shape similar to the one illustrated in FIG. 5A, right oriented, is particularly suited for debridement of medium implant threads.

Figure 5B:
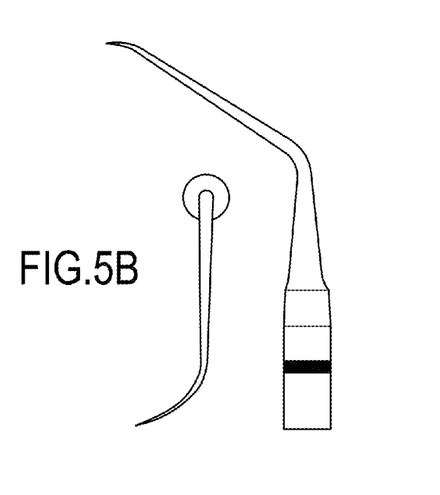

A tip with shape similar to the one illustrated in FIG. 5B, left oriented but pointed, is particularly suited for debridement of narrow implant threads.

Many other shapes may of course be contemplated within the scope and spirit of the present invention.

Titanium is a relatively elastic material which makes of titanium a not intuitive candidate for forming ultrasonic tips. By way of comparison, the elasticity modulus (Young module) for a titanium ultrasonic tip and a stainless steel ultrasonic tip is respectively 114 GPa and 203 GPa. The more elastic, the hardest it becomes for the distal end of the ultrasonic tip to transmit ultrasonic vibrations to an implant to be treated (for a same surface of contact in both cases).

Furthermore, for identical geometrical specifications, a titanium ultrasonic tip shows a resonance frequency higher than the one of a stainless steel ultrasonic tip.

In a particular embodiment, the structural (or geometrical) specifications of the ultrasonic tip are arranged such that said ultrasonic tip has a unique resonance frequency which falls within the operating frequency range of the ultrasonic instrument. The unique resonance frequency at which the ultrasonic tip vibrates and which is transmitted to the implant surface is for instance comprised between 30 kHz and 34 kHz.

Figure 6A:
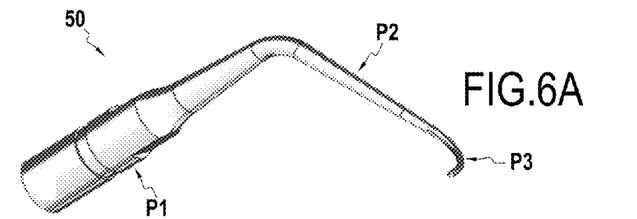
FIGS. 6A and 6B show a configuration of an ultrasonic tip according to a particular embodiment.
Figure 6B:
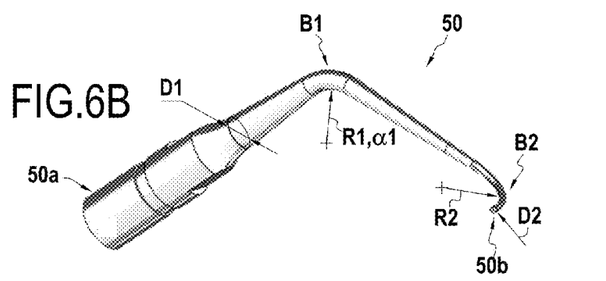

FIGS. 6A and 6B show an exemplary embodiment of an ultrasonic tip 50 according to the present invention, wherein the resonance frequency of the tip is within a range of 33 to 34 kHz. In a particular embodiment, the ultrasonic tip is formed by three successive portions connected to each other from the proximal end towards the distal end of the tip. As shown for instance in FIG. 6A, the exemplary ultrasonic tip 50 comprises:
- a coupling portion P1 configured to mechanically couple with the locking mechanism 24 of the ultrasonic instrument 16;
- a working portion P3 located at the distal end 50b of the ultrasonic tip 50, the working portion P3 being designed to contact an area to be treated so as to transmit ultrasonic vibrations thereto;
- a transitory portion P2 which is an intermediate portion connecting the coupling portion P1 to the working portion P3.

To ensure that the titanium ultrasonic tip of the present disclosure transmit ultrasonic vibrations to the dental surface under treatment in optimal conditions, particular dimensional specifications have been determined by the Applicant.

Considering for instance the embodiment of the ultrasonic tip 50 in FIGS. 6A and 6B, the part of the ultrasonic tip formed by the transitory portion P2 and the working portion P3 has a conic (or truncated cone) shape wherein the base diameter D1 is comprised between 2 mm and 2.5 mm (for instance D1=2.4 mm) and the diameter D2 at the distal end 50b is comprised between 0.2 mm and 0.8 mm (for instance, D2=0.3 mm).

In a particular embodiment, the ultrasonic tip of the present invention comprises a plurality of bends formed in the transitory portion and/or in the working portion of the tip. In a particular embodiment, the ultrasonic tip includes two bends B1 and B2 as shown for instance in FIG. 6B.

As shown also in FIG. 6B, the working portion P3 of the ultrasonic tip can be formed by one bend.

In the embodiment of FIG. 6B, the bends B1 and B2 are designed as follows:
bend B1: the radius R1 is comprised between 2 and 4 mm, and the tilt angle α1 is comprised between 120° and 130°;
bend B2: the radius R2 is comprised between 4 and 6 mm.

Figure 7:
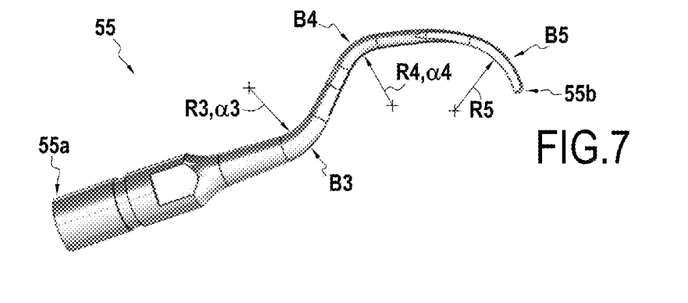
FIG. 7 shows an ultrasonic embodiment according to another particular embodiment.

In another embodiment illustrated in FIG. 7, the entire body of the ultrasonic tip 55 extends within a same plan. The ultrasonic tip 55 includes three bends noted successively B3, B4 and B5 from proximal end 55a to distal end 55b.

In the embodiment of FIG. 7, the bends B3, B4 and B5 are designed as follows:
bend B3: the radius R3 is comprised between 2 and 4 mm, and the tilt angle α3 is comprised between 135° and 140°;
bend B4: the radius R4 is comprised between 3 and 4 mm, and the tilt angle α4 is comprised between 135° and 140;
bend B5: the radius R5 is comprised between 4 and 6 mm.

The ultrasonic tip of the present disclosure is particularly applicable for use in the prophylactic and periodontal care of dental implants most of which are made of titanium.

The invention claimed is:

1. A method of dental treatment of peri-implantitis using an ultrasonic tip operable to cooperate with an ultrasonic instrument to transmit ultrasonic vibrations to a surface of a dental implant to be treated,
wherein said implant and said ultrasonic tip are in titanium, and
wherein a distal portion of the ultrasonic tip includes titanium or pure titanium.

2. The method of claim 1, wherein said ultrasonic tip is made of titanium of the grade 4 type according to standards ISO 5832-2 and ASTM F-67.

3. The method of claim 1, wherein the implant surface includes a threading region comprising a plurality of threads, the distal end of the ultrasonic tip being shaped to be in correspondence with a profile of a recessed region between each pair of threads within the threading region.

4. The method of claim 1, wherein the structural specifications of said ultrasonic tip are arranged such that said ultrasonic tip has a unique resonance frequency which falls within an operating frequency range of said ultrasonic instrument.

5. The method of claim 4, wherein said unique resonance frequency at which are transmitted the ultrasonic vibrations to the implant surface is comprised between 30 kHz and 34 kHz.

6. An ultrasonic tip operable to cooperate with an ultrasonic instrument to vibrate at an ultrasonic frequency for use in dental treatment of peri-implantitis on a dental implant, wherein said ultrasonic tip is made of pure titanium.

7. The ultrasonic tip of claim 6, wherein said ultrasonic tip is made of titanium of the grade 4 type according to the standards ISO 5832-2 and ASTM F-67.

8. The ultrasonic tip of claim 6, wherein the distal end of the ultrasonic tip is formed so as to have any one of a pointed shape, a half-spherical shape and a curved shape.

9. An ultrasonic system for treatment of peri-implantitis, said ultrasonic system comprising:
an ultrasonic tip according to claim 6; and
an ultrasonic instrument operable to transmit ultrasonic vibrations to the ultrasonic tip when said ultrasonic tip is mechanically coupled with said ultrasonic instrument.

10. The ultrasonic system of claim 9, further comprising an ultrasonic generator coupled with said ultrasonic instrument to supply a driving ultrasonic signal within a range of 20 kHz to 40 kHz to said ultrasonic instrument so as to cause ultrasonic vibrations of said ultrasonic tip.

11. The method of claim 1, wherein the ultrasonic tip is made of pure titanium.

12. The method of claim 1, wherein a distal portion of the ultrasonic tip includes grade 4 titanium according to standards ISO 5832-2 and/or ASTM F-67.

13. The method of claim 1, wherein a distal end of the ultrasonic tip has a shape that corresponds with a profile of a recessed region between pairs of threads of a threading region of the dental implant.

14. The method of claim 13, wherein at least the distal end of the ultrasonic tip includes titanium or pure titanium.

15. The ultrasonic tip according to claim 6, wherein a distal portion of the ultrasonic tip includes the pure titanium.

16. The ultrasonic tip according to claim 6, wherein a distal portion of the ultrasonic tip includes grade 4 titanium according to standards ISO 5832-2 and/or ASTM F-67.

17. The ultrasonic tip according to claim 6, wherein a distal end of the ultrasonic tip has a shape that corresponds with a profile of a recessed region between pairs of threads of a threading region of the dental implant.

18. The ultrasonic tip according to claim 17, wherein at least the distal end of the ultrasonic tip includes titanium or pure titanium.

19. An ultrasonic tip configured to cooperate with an ultrasonic instrument to transmit ultrasonic vibrations to a surface of a dental implant to be treated, said ultrasonic tip comprising
    a tip portion configured to be coupled to the ultrasonic instrument, the tip portion of the ultrasonic tip being configured to contact the surface of the dental implant wherein the tip portion includes titanium or pure titanium.

\* \* \* \* \*